(12) United States Patent
Bogosian et al.

(10) Patent No.: US 6,828,124 B2
(45) Date of Patent: Dec. 7, 2004

(54) RECOMBINANT DNA VECTORS FOR EXPRESSION OF SOMATOTROPINS

(75) Inventors: Gregg Bogosian, Clarkson Valley, MO (US); Julia P. O'Neil, St. Louis, MO (US); Noelle D. Aardema, Dana Point, CA (US)

(73) Assignee: Monsanto Technology LLC, St. Louis, MO (US)

( * ) Notice: Subject to any disclaimer, the term of this patent is extended or adjusted under 35 U.S.C. 154(b) by 184 days.

(21) Appl. No.: 10/173,082

(22) Filed: Jun. 17, 2002

(65) Prior Publication Data

US 2003/0166157 A1 Sep. 4, 2003

Related U.S. Application Data

(63) Continuation-in-part of application No. PCT/US01/49977, filed on Dec. 21, 2001.
(60) Provisional application No. 60/258,291, filed on Dec. 26, 2000.

(51) Int. Cl.$^7$ .................. C12P 21/06; C11N 15/09; C12N 15/18; A61K 38/00; A61K 38/27
(52) U.S. Cl. ............. 435/69.1; 435/69.4; 435/252.1; 435/252.33; 435/320.1; 530/300; 530/324
(58) Field of Search ................. 435/69.1, 69.4, 435/252.1, 252.33, 243, 320.1; 530/300, 324

(56) References Cited

U.S. PATENT DOCUMENTS

| 5,254,463 A | 10/1993 | de Boer et al. |
| 5,260,201 A | 11/1993 | de Boer et al. |

FOREIGN PATENT DOCUMENTS

| EP | 0 047 600 B1 | 2/1992 |
| EP | 0 534 705 A2 | 3/1993 |
| EP | 0 547 873 A2 | 6/1993 |
| WO | WO 00/60103 | 10/2000 |

OTHER PUBLICATIONS

Wells (Sep. 18, 1990) "Additivity of Mutational Effects in Proteins." Biochemistry 29(37): 8509–8517.*
Ngo et al. (Mar. 2, 1995) "The Protein Folding Problem and Tertiary Structure Prediction, Chapter 14: Computational Complexity Protein Structure Prediction, and the Levinthal Paradox" pp. 433–506.*
Bork (2000) "Powers and Pitfalls in Sequence Analysis: The 70% Hurdle." Genome Research 10:398–400.*
Skolnick and Fetrow (2000) "From gene to protein structure and function: novel applications of computational approaches in th genomic era." Trends in Biotech. 18(1): 34–39.*
Doerks et al. (Jun. 1998) "Protein annotation: detective work for function prediction." Trends in Genetics 14(6): 248–250.*
Smith and Zhang (Nov. 1997) "The challenges of genome sequence annotation or 'The devil is in the details'." Nature Biotechnology 15:1222–1223.*
Brenner (Apr. 1999) "Errors in genome annotation." Trends in Genetics 15(4): 132–133.*
Bork and Bairoch (Oct. 1996) "Go hunting in sequence databases but watch out for the traps." Trends in Genetics 12(10): 425–427.*
Bogosian, G. et al. "Biosynthesis and incorporation into protein of norleucine by Escherichia coli," *J. of Biol. Chem.*, 264:531–539 (1989).
Seeburg, P.H. et al., "Efficient bacterial expression of bovine and porcine growth hormones." *DNA*, 2:37–45 (1983).
George, H.J. et al. "High–level expression in *Escherichia coli* of biologically active bovine growth hormone" *DNA* 4:273–281, 1985.
Klein, B.K. et al. "Secretion of Active Bovine Somatotropin in *Escherichia coli*" *Bio/Technology* 9:869–872, 1991.
International Search Report for PCT/US01/49977 dated Jun. 11, 2003.

* cited by examiner

Primary Examiner—Brenda Brumback
Assistant Examiner—Christopher James Nichols
(74) Attorney, Agent, or Firm—Grace L. Bonner; Howrey Simon Arnold & White, LLP

(57) ABSTRACT

A family of somatotropin vectors with which microorganisms, preferably bacteria such as, but not limited to *E. coli*, can be transformed to enable the expression of bovine somatotropin at high levels using conventional fermentation and induction conditions.

6 Claims, 2 Drawing Sheets

```
                                    cpex-20 promoter
pXT674   1  GAATTCTACTGTATGAGCATACAGTTAAGGGTTGACAACCGATATTTATT   50
            ||||||||||||||||||||||||||||||||||||||||||||||||||
pXT709   1  GAATTCTACTGTATGAGCATACAGTTAAGGGTTGACAACCGATATTTATT   50 dps RBS
        51  CACTTAATATATAAATATCAACTGAGGCGCGCCCATAACATCAAGAGGAT  100
            ||||||||||||||||||||||||||||||||||||||||||||||||||
        51  CACTTAATATATAAATATCAACTGAGGCGCGCCCATAACATCAAGAGGAT  100

SFE 2531
       101  ATGAAATTATGTTTCCAGCCATGAGCTTGTCCGGACTCTTTGCCAATGCT  150
            ||||||||||||||||||||||||||||||||||||||||||||||||||
       101  ATGAAATTATGTTTCCAGCCATGAGCTTGTCCGGACTCTTTGCCAATGCT  150

SBE→
       151  GTACTCCGGGCTCAGCACCTGCATCAGCTGGCTGCTGACACCTTCAAAGA  200
            ||||||||||||||||||||||||||||||||||||||||||||||||||
       151  GTACTCCGGGCTCAGCACCTGCATCAGCTGGCTGCTGACACCTTCAAAGA  200

201  GTTTGAGCGCACCTACATCCCGGAGGGACAGAGATACTCCATCCAGAACA  250
            |||||||||||||||||||||||||||||| | ||||||||||||||||
       201  GTTTGAGCGCACCTACATCCCGGAGGGACAGCGTTACTCCATCCAGAACA  250

251  CCCAGGTTGCCTTCTGCTTCTCTGAAACCATCCCGGCCCCCACGGGCAAG  300
            |||||||||||||||||||||||||||||||||||||||||| |||||||
       251  CCCAGGTTGCCTTCTGCTTCTCTGAAACCATCCCGGCCCCGACGGGCAAG  300

301  AATGAGGCCCAGCAGAAATCAGACTTGGAGCTGCTTCGCATCTCACTGCT  350
            ||||||||||||||||||||||||||||||||||||||||||||||||||
       301  AATGAGGCCCAGCAGAAATCAGACTTGGAGCTGCTTCGCATCTCACTGCT  350

351  CCTCATCCAGTCGTGGCTTGGGCCCCTGCAGTTCCTCAGCAGAGTCTTCA  400
            ||||||| |   |||||||||| ||||||||||||||||||  ||||||
       351  CCTCATCCAGAGCTGGCTTGGGCCGCTGCAGTTCCTCAGCCGTGTCTTCA  400

401  CCAACAGCTTGGTGTTTGGCACCTCGGACCGTGTCTATGAGAAGCTGAAG  450
            ||||||||||||||||||||||||   |||||||||||||||||||||||
       401  CCAACAGCTTGGTGTTTGGCACCAGCGACCGTGTCTATGAGAAGCTGAAG  450

451  GACCTGCAGGAAGGCATCCTGGCCCTGATGCGGGAGCTGGAAGATGGCAC  500
            |||||||||||||||||||||||||||||||| |||||||||||||||||
       451  GACCTGGAGGAAGGCATCCTGGCCCTGATGCGTGAGCTGGAAGATGGCAC  500
```

FIG. 1A

```
501  CCCCCGGGCTGGGCAGATCCTCAAGCAGACCTATGACAAATTTGACACAA  550
     ||| || |||| ||||||||||||||||||||||||||||||||||||||
501  CCCGCGTGCTGGGCAGATCCTCAAGCAGACCTATGACAAATTTGACACAA  550

551  ACATGCGCAGTGACGACGCGCTGCTCAAGAACTACGGTCTGCTCTCCTGC  600
     ||||||||||||||||||||||||||||||||||||||||||||||||||
551  ACATGCGCAGTGACGACGCGCTGCTCAAGAACTACGGTCTGCTCTCCTGC  600

601  TTCCGGAAGGACCTGCATAAGACGGAGACGTACCTGAGGGTCATGAAGTG  650
     ||||| ||||||||||||||||||||||||||||||||| |||||||||
601  TTCCGTAAGGACCTGCATAAGACGGAGACGTACCTGCGTGTCATGAAGTG  650

Stop Codons  Terminator→
651  CCGCCGCTTCGGGGAGGCCAGCTGCGCCTTCTAGAAGCTTAATT.....C  695
     |||||||||||||||| |||||| |||||| ||| || |
651  CCGCCGCTTCGGGGAGGCGAGCTGCGCCTTCTAATAGCTCGAGTCTAGAC  700

696  TCACTCATTAGGCACCCCAGGCTTTACACTTTATGCTTCCGGCTCGTATA  745
     ||||||||||||||||||||||||||||||||||||||||||||||||||
701  TCACTCATTAGGCACCCCAGGCTTTACACTTTATGCTTCCGGCTCGTATA  750

746  ATGTGTGGAATTGTGAGCGGATAACAATTTCACACAGGAAACAGCTGATT  795
     |||||||||||||||||||||||||||||||||||||||| |||||||||
751  ATGTGTGGAATTGTGAGCGGATAACAATTTCACACAGGAAAAAGCTGATT  800

796  GCCCTTCACCGCCTGGCCTCCGTTGAGCCATCTGGATCGGCAGCGTTGTC  845
     ||||||||||||||||||||||||||||||||||||||||||||||||||
801  GCCCTTCACCGCCTGGCCTCCGTTGAGCCATCTGGATCGGCAGCGTTGTC  850

846  TTCATCAACCGGAACGAGCATGCCGGAGAGCAGCTCACTCATTAGGCACC  895
     ||||||||||||||||||||||||||||||||||||||||||||||||||
851  TTCATCAACCGGAACGAGCATGCCGGAGAGCAGCTCACTCATTAGGCACC  900

896  CCAGGCTTTACACTTTATGCTTCCGGCTCGTATAATGTGTGGAATTGTGA  945
     ||||||||||||||||||||||||||||||||||||||||||||||||||
901  CCAGGCTTTACACTTTATGCTTCCGGCTCGTATAATGTGTGGAATTGTGA  950

End of terminator
946  GCGGATAACAATTTCACACAGGAAACAGAATTAAGCTT  983
     ||| |||||||||||||||||||            |||||
951  GCGGATAACAATTTCACACAG...........AAGCTT  977
```

FIG. 1B

RECOMBINANT DNA VECTORS FOR EXPRESSION OF SOMATOTROPINS

CROSS-REFERENCE TO RELATED APPLICATIONS

In accordance with 35 U.S.C. §§119(e) and 365(c) this continuation-in-part application claims the benefit of the filing date of co-pending international application PCT/US01/49977, with an international filing date of Dec. 21, 2001, which claims the benefit of U.S. provisional application No. 60/258,291, filed Dec. 26, 2000, the entirety of each of which is herein incorporated by reference.

BACKGROUND OF THE INVENTION

In mammals, growth hormones (somatotropins) are initially expressed in a pre-hormone form comprising a leader sequence which is removed during secretion of the mature, biologically active hormone from pituitary cells. As used herein, "mature" somatotropin ("ST") means having an amino acid length essentially like those of the ST secreted into the bloodstream of the animal, e.g., N-Ala-Phe-Pro- or N-Phe-Pro-bovine ST, N-Phe-Pro-human, -porcine (identical to canine) or -equine ST, etc.

Attempts to bacterially express human and bovine STs in non-secretion systems using structural genes having the sequences of their cDNAs were at first unsuccessful. Researchers succeeded after introducing silent mutations into the front end of the structural gene. P. H. Seeburg et al., attributed the original difficulties to translation being impeded by secondary structure of the mRNA corresponding to cDNA, and taught lessening such secondary structure to enable significant expression. DNA, Vol. 2, No. 1, 1983, pp. 37–45; U.S. Pat. Nos. 5,254,463 and 5,260,201.

It has been possible to obtain commercially viable ST expression levels using DNA containing certain silent mutations. However, the need for new vectors that are highly productive and less expensive to use has been difficult to satisfy because the relationships between the configurations and expression levels of "mature" somatotropin vectors remain poorly understood and highly unpredictable.

SUMMARY OF THE INVENTION

Described herein is a family of ST vectors with which micro-organisms, preferably bacteria such as, but not limited to E. coli, can be transformed to enable the expression of bovine ST ("bST") at high levels using conventional fermentation and induction conditions. This family is exemplified by the 44 vectors listed in Table I each of which comprises the corresponding sequence of SEQ ID NOs 1 through 44, as indicated in Table I. Each of SEQ ID NOs 1 through 44, extends from an EcoRI site (GAATTC) before the promoter region, through the promoter, ribosome binding site ("RBS") and entire bST structural gene, ending with the translation stop codon for the structural gene.

BRIEF DESCRIPTION OF THE DRAWINGS

FIGS. 1A/1B: DNA sequence comparison of fragments of the expression vectors pXT674 (SEQ ID NO:49) and pXT709 (SEQ ID NO:50).

DETAILED DESCRIPTION OF THE INVENTION

Each of the vectors having SEQ ID NOs 1–44 includes a synthetic promoter, herein designated "cpex-20", which is disclosed in PCT Appln. PCT/US00/40014 filed Mar. 31, 2000, which claims priority of U.S. Provisional Patent Appln. No. 60/127,449, filed Apr. 1, 1999. This promoter is situated between the EcoRI site (GAATTC) and the AscI site (GGCGCGCC). Various other conventional and novel promoters can be used in these vectors in lieu of cpex-20 to achieve good levels of ST expression.

To construct the expression vector pXT709, the synthetic EcoRI-HindIII DNA fragment shown in FIGS. 1A/1B: (SEQ ID NO:50) was ligated into pBR322 (Boehringer Mannheim, Indianapolis, Ind.) which had been digested with EcoRI and HindIII. The resulting plasmid, designated pXT709, was then transformed into recA+ E. coli K-12 host strain and somatotropin production was induced with nalidixic acid.

To construct similar plasmids comprising the other sequences listed in the Sequence Listing (namely SEQ ID NOs 1–15, and 17–44), the corresponding synthetic DNA fragments could be similarly prepared and ligated into pBR322. Furthermore, the many other techniques and/or procedures for ligating the described DNA fragments, as shown in the Sequence Listing, into various other plasmids are known and routinely practiced by those of ordinary skill in the art. Moreover, plasmids suitable for transforming E. coli and/or other bacteria so as to achieve somatotropin production from cultures of the transformed bacteria are known and regularly used by ordinarily skilled artisans.

SEQ ID NOs 1–17 have an identical RBS, CATAACAT-CAAGAGGATATGAAATT (SEQ ID NO:45), herein designated "dps", that is native to E. coli. SEQ ID NOs 18–29 share a novel synthetic RBS, GTACAAATCATAGAGGG-TATTTAAT (SEQ ID NO:46) which is herein designated "L49". SEQ ID NOs 30–42 share a second novel synthetic RBS, AGACACTAAATAGAGGGTATTTAATT (SEQ ID NO:47) herein designated "L437". Seq. Nos. 43–44 share a third novel synthetic RBS, TAAAAGAGACTAGGAG-GAGATTAGA (SEQ ID NO:48), herein designated "R806". Each RBS is situated between the AscI site and the ATG translation start codon of the bST structural gene. The AscI site begins at coordinate 76 of each sequence. The ATG start codon begins at approximately coordinate 109; this can vary slightly due to the RBSs employed having slightly different lengths.

All of the vectors listed in Table I (respectively comprising SEQ ID NOS 1–44) have structural genes that differ from cDNA encoding "mature" bST by containing various arrays of silent changes within the nucleotides encoding the first 16 codons of bST. As shown in FIGS. 1A/1B, vector pXT709 (SEQ ID NO: 50) differs from pXT674 (SEQ ID NO: 49) by having an additional 12 codons within the structural gene changed from those of cDNA, 11 to E. coli-preferred codons and a twelfth to eliminate an undesirable restriction site, by changing the translation stop codon to two tandem stop codons, and by substituting a different terminator which has two lacUV5 promoters in tandem. pXT703 (comprising SEQ ID NO:15) and pXT747 (comprising SEQ ID NO:17) differ from pXT601 (comprising SEQ ID NO:2) and pXT686 (comprising SEQ ID NO:13), respectively, in the same way.

Each of the vectors comprising SEQ ID NOs 1 through 44 have expressed mature bST at unoptimized levels of at least about 3.5 grams/liter ("gm/l"), most of them above 4.5 gm/l, and some at 7 gm/l or higher, using the fermentation conditions described in Bogosian et al., J. Biol. Chem., vol. 264, pp. 531–39, Jan. 5, 1989, except that 50 ppm of nalidixic acid was used as the inducer instead of indole acrylic acid.

The expression levels of mature ST vectors are very unpredictable from published teachings, e.g., P. H. Seeburg et al. In fact, the vectors comprising the sequences of SEQ ID NOs 1 through 17, 30 through 35, and 37 through 42 have been found, using calculations as recommended in Seeburg et al., to have mRNA secondary structure greater than, rather than lessened from that of bST cDNA.

TABLE I

| SEQ ID NO | RBS | pXT |
|---|---|---|
| 1 | dps | 600 |
| 2 | dps | 601 |
| 3 | dps | 602 |
| 4 | dps | 658 |
| 5 | dps | 670 |
| 6 | dps | 672 |
| 7 | dps | 673 |
| 8 | dps | 674 |
| 9 | dps | 675 |
| 10 | dps | 676 |
| 11 | dps | 682 |
| 12 | dps | 683 |
| 13 | dps | 686 |
| 14 | dps | 689 |
| 15 | dps | 703 |
| 16 | dps | 709 |
| 17 | dps | 747 |
| 18 | L49 | 487 |
| 19 | L49 | 536 |
| 20 | L49 | 541 |
| 21 | L49 | 542 |

TABLE I-continued

| SEQ ID NO | RBS | pXT |
|---|---|---|
| 22 | L49 | 548 |
| 23 | L49 | 549 |
| 24 | L49 | 562 |
| 25 | L49 | 576 |
| 26 | L49 | 579 |
| 27 | L49 | 580 |
| 28 | L49 | 581 |
| 29 | L49 | 584 |
| 30 | L437 | 491 |
| 31 | L437 | 529 |
| 32 | L437 | 530 |
| 33 | L437 | 619 |
| 34 | L437 | 605 |
| 35 | L437 | 606 |
| 36 | L437 | 607 |
| 37 | L437 | 620 |
| 38 | L437 | 631 |
| 39 | L437 | 632 |
| 40 | L437 | 633 |
| 41 | L437 | 635 |
| 42 | L437 | 681 |
| 43 | R806 | 483 |
| 44 | R806 | 564 |

We claim:

1. A vector useful for expressing mature bovine somatotropin in *E. coli* and comprising a DNA sequence selected from the group consisting of SEQ ID NOs 2, 8, 13, 16, 19, 27, 30, 41, and 44.

2. A vector of claim 1 comprising a DNA sequence selected from the group consisting of SEQ ID NOs 2, 8, 13, 16, 30, and 41.

3. A vector of claim 1 comprising a DNA sequence consisting essentially of SEQ ID NO:16.

4. *E. coli* transformed with a vector of claim 1, 2, or 3.

5. A process for making mature bovine somatotropin comprising fermenting an *E. coli* of claim 4 and inducing expression of the somatotropin.

6. A vector of claim 1 comprising the DNA sequence of SEQ ID NO:16.

* * * * *

```
                        SEQUENCE LISTING

<160> NUMBER OF SEQ ID NOS: 50

<210> SEQ ID NO 1
<211> LENGTH: 684
<212> TYPE: DNA
<213> ORGANISM: Artificial Sequence
<220> FEATURE:
<223> OTHER INFORMATION: Somatotropin expression vector pXT 600

<400> SEQUENCE: 1
gaattctact gtatgagcat acagttaagg gttgacaacc gatatttatt cacttaatat      60
ataaatatca actgaggcgc gcccataaca tcaagaggat atgaaattat gttcccagca     120
atgagcttgt ccggactttt tgcaaatgct gtgctccggg ctcagcacct gcatcagctg     180
gctgctgaca ccttcaaaga gtttgagcgc acctacatcc cggagggaca gagatactcc     240
atccagaaca cccaggttgc cttctgcttc tctgaaacca tcccggcccc cacgggcaag     300
aatgaggccc agcagaaatc agacttggag ctgcttcgca tctcactgct cctcatccag     360
tcgtggcttg gcccctgca gttcctcagc agagtcttca ccaacagctt ggtgtttggc     420
acctcggacc gtgtctatga aagctgaag gacctggagg aaggcatcct ggccctgatg     480
cgggagctgg aagatggcac ccccgggct gggcagatcc tcaagcagac ctatgacaaa     540
tttgacacaa acatgcgcag tgacgacgcg ctgctcaaga actacggtct gctctcctgc     600
```

-continued

```
ttccggaagg acctgcataa gacggagacg tacctgaggg tcatgaagtg ccgccgcttc    660
ggggaggcca gctgcgcctt ctag                                           684
```

<210> SEQ ID NO 2
<211> LENGTH: 684
<212> TYPE: DNA
<213> ORGANISM: Artificial Sequence
<220> FEATURE:
<223> OTHER INFORMATION: Somatotropin expression vector pXT 601

<400> SEQUENCE: 2

```
gaattctact gtatgagcat acagttaagg gttgacaacc gatatttatt cacttaatat     60
ataaatatca actgaggcgc gcccataaca tcaagaggat atgaaattat gtttccagcc    120
atgtcattgt ccggactgtt tgcgaacgct gtgctccggg ctcagcacct gcatcagctg    180
gctgctgaca ccttcaaaga gtttgagcgc acctacatcc cggagggaca gagatactcc    240
atccagaaca cccaggttgc cttctgcttc tctgaaacca tcccggcccc cacgggcaag    300
aatgaggccc agcagaaatc agacttggag ctgcttcgca tctcactgct cctcatccag    360
tcgtggcttg ggcccctgca gttcctcagc agagtcttca ccaacagctt ggtgtttggc    420
acctcggacc gtgtctatga aagctgaag gacctggagg aaggcatcct ggccctgatg    480
cgggagctgg aagatggcac ccccgggct ggcagatcc tcaagcagac ctatgacaaa     540
tttgacacaa acatgcgcag tgacgacgcg ctgctcaaga actacggtct gctctcctgc    600
ttccggaagg acctgcataa gacggagacg tacctgaggg tcatgaagtg ccgccgcttc    660
ggggaggcca gctgcgcctt ctag                                           684
```

<210> SEQ ID NO 3
<211> LENGTH: 684
<212> TYPE: DNA
<213> ORGANISM: Artificial Sequence
<220> FEATURE:
<223> OTHER INFORMATION: Somatotropin expression vector pXT602

<400> SEQUENCE: 3

```
gaattctact gtatgagcat acagttaagg gttgacaacc gatatttatt cacttaatat     60
ataaatatca actgaggcgc gcccataaca tcaagaggat atgaaattat gttccctgca    120
atgtcattgt ccggactgtt tgcaaatgcg gtactccggg ctcagcacct gcatcagctg    180
gctgctgaca ccttcaaaga gtttgagcgc acctacatcc cggagggaca gagatactcc    240
atccagaaca cccaggttgc cttctgcttc tctgaaacca tcccggcccc cacgggcaag    300
aatgaggccc agcagaaatc agacttggag ctgcttcgca tctcactgct cctcatccag    360
tcgtggcttg ggcccctgca gttcctcagc agagtcttca ccaacagctt ggtgtttggc    420
acctcggacc gtgtctatga aagctgaag gacctggagg aaggcatcct ggccctgatg    480
cgggagctgg aagatggcac ccccgggct ggcagatcc tcaagcagac ctatgacaaa     540
tttgacacaa acatgcgcag tgacgacgcg ctgctcaaga actacggtct gctctcctgc    600
ttccggaagg acctgcataa gacggagacg tacctgaggg tcatgaagtg ccgccgcttc    660
ggggaggcca gctgcgcctt ctag                                           684
```

<210> SEQ ID NO 4
<211> LENGTH: 684
<212> TYPE: DNA
<213> ORGANISM: Artificial sequence
<220> FEATURE:
<223> OTHER INFORMATION: Somatotropin expression vector pXT 658

-continued

<400> SEQUENCE: 4

```
gaattctact gtatgagcat acagttaagg gttgacaacc gatatttatt cacttaatat      60
ataaatatca actgaggcgc gcccataaca tcaagaggat atgaaattat gttcccagca     120
atgtcattgt ccggactctt tgcaaatgcg gtgctccggg ctcagcacct gcatcagctg     180
gctgctgaca ccttcaaaga gtttgagcgc acctacatcc cggagggaca gagatactcc     240
atccagaaca cccaggttgc cttctgcttc tctgaaacca tcccggcccc cacgggcaag     300
aatgaggccc agcagaaatc agacttggag ctgcttcgca tctcactgct cctcatccag     360
tcgtggcttg gcccctgca gttcctcagc agagtcttca ccaacagctt ggtgtttggc     420
acctcggacc gtgtctatga aagctgaag gacctggagg aaggcatcct ggccctgatg     480
cgggagctgg aagatggcac ccccgggct gggcagatcc tcaagcagac ctatgacaaa     540
tttgacacaa acatgcgcag tgacgacgcg ctgctcaaga actacggtct gctctcctgc     600
ttccggaagg acctgcataa gacggagacg tacctgaggg tcatgaagtg ccgccgcttc     660
ggggaggcca gctgcgcctt ctag                                            684
```

<210> SEQ ID NO 5
<211> LENGTH: 684
<212> TYPE: DNA
<213> ORGANISM: Artificial Sequence
<220> FEATURE:
<223> OTHER INFORMATION: Somatotropin expression vector pXT 670

<400> SEQUENCE: 5

```
gaattctact gtatgagcat acagttaagg gttgacaacc gatatttatt cacttaatat      60
ataaatatca actgaggcgc gcccataaca tcaagaggat atgaaattat gtttccagcc     120
atgagcttgt ccggattgtt tgcaaacgct gtgctccggg ctcagcacct gcatcagctg     180
gctgctgaca ccttcaaaga gtttgagcgc acctacatcc cggagggaca gagatactcc     240
atccagaaca cccaggttgc cttctgcttc tctgaaacca tcccggcccc cacgggcaag     300
aatgaggccc agcagaaatc agacttggag ctgcttcgca tctcactgct cctcatccag     360
tcgtggcttg gcccctgca gttcctcagc agagtcttca ccaacagctt ggtgtttggc     420
acctcggacc gtgtctatga aagctgaag gacctggagg aaggcatcct ggccctgatg     480
cgggagctgg aagatggcac ccccgggct gggcagatcc tcaagcagac ctatgacaaa     540
tttgacacaa acatgcgcag tgacgacgcg ctgctcaaga actacggtct gctctcctgc     600
ttccggaagg acctgcataa gacggagacg tacctgaggg tcatgaagtg ccgccgcttc     660
ggggaggcca gctgcgcctt ctag                                            684
```

<210> SEQ ID NO 6
<211> LENGTH: 684
<212> TYPE: DNA
<213> ORGANISM: Artificial Sequence
<220> FEATURE:
<223> OTHER INFORMATION: Somatotropin expression vector pXT 672

<400> SEQUENCE: 6

```
gaattctact gtatgagcat acagttaagg gttgacaacc gatatttatt cacttaatat      60
ataaatatca actgaggcgc gcccataaca tcaagaggat atgaaattat gttcccagcc     120
atgtcattgt ccggactgtt tgcaaatgct gtactccggg ctcagcacct gcatcagctg     180
gctgctgaca ccttcaaaga gtttgagcgc acctacatcc cggagggaca gagatactcc     240
```

```
atccagaaca cccaggttgc cttctgcttc tctgaaacca tcccggcccc cacgggcaag    300
aatgaggccc agcagaaatc agacttggag ctgcttcgca tctcactgct cctcatccag    360
tcgtggcttg ggcccctgca gttcctcagc agagtcttca ccaacagctt ggtgtttggc    420
acctcggacc gtgtctatga aagctgaag gacctggagg aaggcatcct ggccctgatg     480
cgggagctgg aagatggcac ccccggggct gggcagatcc tcaagcagac ctatgacaaa    540
tttgacacaa acatgcgcag tgacgacgcg ctgctcaaga actacggtct gctctcctgc    600
ttccggaagg acctgcataa gacggagacg tacctgaggg tcatgaagtg ccgccgcttc    660
ggggaggcca gctgcgcctt ctag                                           684

<210> SEQ ID NO 7
<211> LENGTH: 684
<212> TYPE: DNA
<213> ORGANISM: Artificial Sequence
<220> FEATURE:
<223> OTHER INFORMATION: Somatotropin expression vector pXT 673

<400> SEQUENCE: 7
gaattctact gtatgagcat acagttaagg gttgacaacc gatatttatt cacttaatat     60
ataaatatca actgaggcgc gcccataaca tcaagaggat atgaaattat gttcccagcc    120
atgagcttgt ccggactgtt tgccaacgct gtcctccggg ctcagcacct gcatcagctg    180
gctgctgaca ccttcaaaga gtttgagcgc acctacatcc cggagggaca gagatactcc    240
atccagaaca cccaggttgc cttctgcttc tctgaaacca tcccggcccc cacgggcaag    300
aatgaggccc agcagaaatc agacttggag ctgcttcgca tctcactgct cctcatccag    360
tcgtggcttg ggcccctgca gttcctcagc agagtcttca ccaacagctt ggtgtttggc    420
acctcggacc gtgtctatga aagctgaag gacctggagg aaggcatcct ggccctgatg     480
cgggagctgg aagatggcac ccccggggct gggcagatcc tcaagcagac ctatgacaaa    540
tttgacacaa acatgcgcag tgacgacgcg ctgctcaaga actacggtct gctctcctgc    600
ttccggaagg acctgcataa gacggagacg tacctgaggg tcatgaagtg ccgccgcttc    660
ggggaggcca gctgcgcctt ctag                                           684

<210> SEQ ID NO 8
<211> LENGTH: 684
<212> TYPE: DNA
<213> ORGANISM: Artificial Sequence
<220> FEATURE:
<223> OTHER INFORMATION: Somatotropin expression vector pXT 674

<400> SEQUENCE: 8
gaattctact gtatgagcat acagttaagg gttgacaacc gatatttatt cacttaatat     60
ataaatatca actgaggcgc gcccataaca tcaagaggat atgaaattat gtttccagcc    120
atgagcttgt ccggactctt tgccaatgct gtactccggg ctcagcacct gcatcagctg    180
gctgctgaca ccttcaaaga gtttgagcgc acctacatcc cggagggaca gagatactcc    240
atccagaaca cccaggttgc cttctgcttc tctgaaacca tcccggcccc cacgggcaag    300
aatgaggccc agcagaaatc agacttggag ctgcttcgca tctcactgct cctcatccag    360
tcgtggcttg ggcccctgca gttcctcagc agagtcttca ccaacagctt ggtgtttggc    420
acctcggacc gtgtctatga aagctgaag gacctggagg aaggcatcct ggccctgatg     480
cgggagctgg aagatggcac ccccggggct gggcagatcc tcaagcagac ctatgacaaa    540
tttgacacaa acatgcgcag tgacgacgcg ctgctcaaga actacggtct gctctcctgc    600
```

```
ttccggaagg acctgcataa gacggagacg tacctgaggg tcatgaagtg ccgccgcttc     660
ggggaggcca gctgcgcctt ctag                                            684
```

<210> SEQ ID NO 9
<211> LENGTH: 684
<212> TYPE: DNA
<213> ORGANISM: Artificial Sequence
<220> FEATURE:
<223> OTHER INFORMATION: Somatotropin expression vector pXT 675

<400> SEQUENCE: 9

```
gaattctact gtatgagcat acagttaagg gttgacaacc gatatttatt cacttaatat     60
ataaatatca actgaggcgc gcccataaca tcaagaggat atgaaattat gttcccagcc    120
atgagcttgt ccggactgtt tgccaatgct gtactccggg ctcagcacct gcatcagctg    180
gctgctgaca ccttcaaaga gtttgagcgc acctacatcc cggagggaca gagatactcc    240
atccagaaca cccaggttgc cttctgcttc tctgaaacca tcccggcccc cacgggcaag    300
aatgaggccc agcagaaatc agacttggag ctgcttcgca tctcactgct cctcatccag    360
tcgtggcttg ggcccctgca gttcctcagc agagtcttca ccaacagctt ggtgtttggc    420
acctcggacc gtgtctatga aagctgaag gacctggagg aaggcatcct ggccctgatg    480
cgggagctgg aagatggcac ccccccgggct gggcagatcc tcaagcagac ctatgacaaa    540
tttgacacaa acatgcgcag tgacgacgcg ctgctcaaga actacggtct gctctcctgc    600
ttccggaagg acctgcataa gacggagacg tacctgaggg tcatgaagtg ccgccgcttc    660
ggggaggcca gctgcgcctt ctag                                            684
```

<210> SEQ ID NO 10
<211> LENGTH: 684
<212> TYPE: DNA
<213> ORGANISM: Artificial Sequence
<220> FEATURE:
<223> OTHER INFORMATION: Somatotropin expression vector pXT 676

<400> SEQUENCE: 10

```
gaattctact gtatgagcat acagttaagg gttgacaacc gatatttatt cacttaatat     60
ataaatatca actgaggcgc gcccataaca tcaagaggat atgaaattat gtttccagcc    120
atgtccttgt ccggactctt tgccaacgct gtcctccggg ctcagcacct gcatcagctg    180
gctgctgaca ccttcaaaga gtttgagcgc acctacatcc cggagggaca gagatactcc    240
atccagaaca cccaggttgc cttctgcttc tctgaaacca tcccggcccc cacgggcaag    300
aatgaggccc agcagaaatc agacttggag ctgcttcgca tctcactgct cctcatccag    360
tcgtggcttg ggcccctgca gttcctcagc agagtcttca ccaacagctt ggtgtttggc    420
acctcggacc gtgtctatga aagctgaag gacctggagg aaggcatcct ggccctgatg    480
cgggagctgg aagatggcac ccccccgggct gggcagatcc tcaagcagac ctatgacaaa    540
tttgacacaa acatgcgcag tgacgacgcg ctgctcaaga actacggtct gctctcctgc    600
ttccggaagg acctgcataa gacggagacg tacctgaggg tcatgaagtg ccgccgcttc    660
ggggaggcca gctgcgcctt ctag                                            684
```

<210> SEQ ID NO 11
<211> LENGTH: 684
<212> TYPE: DNA
<213> ORGANISM: Artificial Sequence
<220> FEATURE:

<223> OTHER INFORMATION: Somatotropin expression vector pXT 682

<400> SEQUENCE: 11

```
gaattctact gtatgagcat acagttaagg gttgacaacc gatatttatt cacttaatat      60
ataaatatca actgaggcgc gcccataaca tcaagaggat atgaaattat gttcccagcc     120
atgtcattgt ccggactgtt tgcgaacgct gtactccggg ctcagcacct gcatcagctg     180
gctgctgaca ccttcaaaga gtttgagcgc acctacatcc cggagggaca gagatactcc     240
atccagaaca cccaggttgc cttctgcttc tctgaaacca tcccggcccc cacgggcaag     300
aatgaggccc agcagaaatc agacttggag ctgcttcgca tctcactgct cctcatccag     360
tcgtggcttg ggcccctgca gttcctcagc agagtcttca ccaacagctt ggtgtttggc     420
acctcggacc gtgtctatga aagctgaag gacctggagg aaggcatcct ggccctgatg     480
cgggagctgg aagatggcac ccccgggct gggcagatcc tcaagcagac ctatgacaaa     540
tttgacacaa acatgcgcag tgacgacgcg ctgctcaaga actacggtct gctctcctgc     600
ttccggaagg acctgcataa gacggagacg tacctgaggg tcatgaagtg ccgccgcttc     660
ggggaggcca gctgcgcctt ctag                                            684
```

<210> SEQ ID NO 12
<211> LENGTH: 684
<212> TYPE: DNA
<213> ORGANISM: Artificial Sequence
<220> FEATURE:
<223> OTHER INFORMATION: Somatotropin expression vector pXT 683

<400> SEQUENCE: 12

```
gaattctact gtatgagcat acagttaagg gttgacaacc gatatttatt cacttaatat      60
ataaatatca actgaggcgc gcccataaca tcaagaggat atgaaattat gttcccagcc     120
atgtcattgt ccggactctt tgcaaatgct gtgctccggg ctcagcacct gcatcagctg     180
gctgctgaca ccttcaaaga gtttgagcgc acctacatcc cggagggaca gagatactcc     240
atccagaaca cccaggttgc cttctgcttc tctgaaacca tcccggcccc cacgggcaag     300
aatgaggccc agcagaaatc agacttggag ctgcttcgca tctcactgct cctcatccag     360
tcgtggcttg ggcccctgca gttcctcagc agagtcttca ccaacagctt ggtgtttggc     420
acctcggacc gtgtctatga aagctgaag gacctggagg aaggcatcct ggccctgatg     480
cgggagctgg aagatggcac ccccgggct gggcagatcc tcaagcagac ctatgacaaa     540
tttgacacaa acatgcgcag tgacgacgcg ctgctcaaga actacggtct gctctcctgc     600
ttccggaagg acctgcataa gacggagacg tacctgaggg tcatgaagtg ccgccgcttc     660
ggggaggcca gctgcgcctt ctag                                            684
```

<210> SEQ ID NO 13
<211> LENGTH: 684
<212> TYPE: DNA
<213> ORGANISM: Artificial Sequence
<220> FEATURE:
<223> OTHER INFORMATION: Somatotropin expression vector pXT 686

<400> SEQUENCE: 13

```
gaattctact gtatgagcat acagttaagg gttgacaacc gatatttatt cacttaatat      60
ataaatatca actgaggcgc gcccataaca tcaagaggat atgaaattat gttcccagcc     120
atgtcattgt ccggactctt tgcgaacgct gtactccggg ctcagcacct gcatcagctg     180
gctgctgaca ccttcaaaga gtttgagcgc acctacatcc cggagggaca gagatactcc     240
```

```
atccagaaca cccaggttgc cttctgcttc tctgaaacca tcccggcccc cacgggcaag    300
aatgaggccc agcagaaatc agacttggag ctgcttcgca tctcactgct cctcatccag    360
tcgtggcttg ggcccctgca gttcctcagc agagtcttca ccaacagctt ggtgtttggc    420
acctcggacc gtgtctatga agctgaagg gacctggagg aaggcatcct ggccctgatg    480
cgggagctgg aagatggcac ccccgggct gggcagatcc tcaagcagac ctatgacaaa    540
tttgacacaa acatgcgcag tgacgacgcg ctgctcaaga actacggtct gctctcctgc    600
ttccggaagg acctgcataa gacgagacg tacctgaggg tcatgaagtg ccgccgcttc    660
ggggaggcca gctgcgcctt ctag                                          684

<210> SEQ ID NO 14
<211> LENGTH: 684
<212> TYPE: DNA
<213> ORGANISM: Artificial Sequence
<220> FEATURE:
<223> OTHER INFORMATION: Somatotropin expression vector pXT 689

<400> SEQUENCE: 14
gaattctact gtatgagcat acagttaagg gttgacaacc gatatttatt cacttaatat     60
ataaatatca actgaggcgc gcccataaca tcaagaggat atgaaattat gtttccagcc    120
atgtcattgt ccggactgtt tgcaaacgct gtgctccggg ctcagcacct gcatcagctg    180
gctgctgaca ccttcaaaga gtttgagcgc acctacatcc cggagggaca gagatactcc    240
atccagaaca cccaggttgc cttctgcttc tctgaaacca tcccggcccc cacgggcaag    300
aatgaggccc agcagaaatc agacttggag ctgcttcgca tctcactgct cctcatccag    360
tcgtggcttg ggcccctgca gttcctcagc agagtcttca ccaacagctt ggtgtttggc    420
acctcggacc gtgtctatga agctgaagg gacctggagg aaggcatcct ggccctgatg    480
cgggagctgg aagatggcac ccccgggct gggcagatcc tcaagcagac ctatgacaaa    540
tttgacacaa acatgcgcag tgacgacgcg ctgctcaaga actacggtct gctctcctgc    600
ttccggaagg acctgcataa gacgagacg tacctgaggg tcatgaagtg ccgccgcttc    660
ggggaggcca gctgcgcctt ctag                                          684

<210> SEQ ID NO 15
<211> LENGTH: 687
<212> TYPE: DNA
<213> ORGANISM: Artificial Sequence
<220> FEATURE:
<223> OTHER INFORMATION: Somatotropin expression vector pXT 703

<400> SEQUENCE: 15
gaattctact gtatgagcat acagttaagg gttgacaacc gatatttatt cacttaatat     60
ataaatatca actgaggcgc gcccataaca tcaagaggat atgaaattat gtttccagcc    120
atgtcattgt ccggactgtt tgcgaacgct gtgctccggg ctcagcacct gcatcagctg    180
gctgctgaca ccttcaaaga gtttgagcgc acctacatcc cggagggaca gcgttactcc    240
atccagaaca cccaggttgc cttctgcttc tctgaaacca tcccggcccc gacgggcaag    300
aatgaggccc agcagaaatc agacttggag ctgcttcgca tctcactgct cctcatccag    360
agctggcttg ggccgctgca gttcctcagc cgtgtcttca ccaacagctt ggtgtttggc    420
accagcgacc gtgtctatga agctgaagg gacctggagg aaggcatcct ggccctgatg    480
cgtgagctgg aagatggcac cccgcgtgct gggcagatcc tcaagcagac ctatgacaaa    540
```

```
tttgacacaa acatgcgcag tgacgacgcg ctgctcaaga actacggtct gctctcctgc    600
ttccgtaagg acctgcataa gacggagacg tacctgcgtg tcatgaagtg ccgccgcttc    660
ggggaggcga gctgcgcctt ctaatag                                        687

<210> SEQ ID NO 16
<211> LENGTH: 687
<212> TYPE: DNA
<213> ORGANISM: Artificial Sequence
<220> FEATURE:
<223> OTHER INFORMATION: Somatotropin expression vector pXT 709

<400> SEQUENCE: 16
gaattctact gtatgagcat acagttaagg gttgacaacc gatatttatt cacttaatat     60
ataaatatca actgaggcgc gcccataaca tcaagaggat atgaaattat gtttccagcc    120
atgagcttgt ccggactctt tgccaatgct gtactccggg ctcagcacct gcatcagctg    180
gctgctgaca ccttcaaaga gtttgagcgc acctacatcc cggagggaca gcgttactcc    240
atccagaaca cccaggttgc cttctgcttc tctgaaacca tcccggcccc gacgggcaag    300
aatgaggccc agcagaaatc agacttggag ctgcttcgca tctcactgct cctcatccag    360
agctggcttg gccgctgca gttcctcagc cgtgtcttca ccaacagctt ggtgtttggc    420
accagcgacc gtgtctatga aagctgaag gacctggagg aaggcatcct ggccctgatg    480
cgtgagctgg aagatggcac cccgcgtgct gggcagatcc tcaagcagac ctatgacaaa    540
tttgacacaa acatgcgcag tgacgacgcg ctgctcaaga actacggtct gctctcctgc    600
ttccgtaagg acctgcataa gacggagacg tacctgcgtg tcatgaagtg ccgccgcttc    660
ggggaggcga gctgcgcctt ctaatag                                        687

<210> SEQ ID NO 17
<211> LENGTH: 687
<212> TYPE: DNA
<213> ORGANISM: Artificial Sequence
<220> FEATURE:
<223> OTHER INFORMATION: Somatotropin expression vector pXT 747

<400> SEQUENCE: 17
gaattctact gtatgagcat acagttaagg gttgacaacc gatatttatt cacttaatat     60
ataaatatca actgaggcgc gcccataaca tcaagaggat atgaaattat gtttccagcc    120
atgtcattgt ccggactctt tgcgaacgct gtactccggg ctcagcacct gcatcagctg    180
gctgctgaca ccttcaaaga gtttgagcgc acctacatcc cggagggaca gcgttactcc    240
atccagaaca cccaggttgc cttctgcttc tctgaaacca tcccggcccc gacgggcaag    300
aatgaggccc agcagaaatc agacttggag ctgcttcgca tctcactgct cctcatccag    360
agctggcttg gccgctgca gttcctcagc cgtgtcttca ccaacagctt ggtgtttggc    420
accagcgacc gtgtctatga aagctgaag gacctggagg aaggcatcct ggccctgatg    480
cgtgagctgg aagatggcac cccgcgtgct gggcagatcc tcaagcagac ctatgacaaa    540
tttgacacaa acatgcgcag tgacgacgcg ctgctcaaga actacggtct gctctcctgc    600
ttccgtaagg acctgcataa gacggagacg tacctgcgtg tcatgaagtg ccgccgcttc    660
ggggaggcga gctgcgcctt ctaatag                                        687

<210> SEQ ID NO 18
<211> LENGTH: 684
<212> TYPE: DNA
<213> ORGANISM: Artificial Sequence
```

-continued

```
<220> FEATURE:
<223> OTHER INFORMATION: Somatotropin expression vector pXT 487

<400> SEQUENCE: 18
gaattctact gtatgagcat acagttaagg gttgacaacc gatatttatt cacttaatat      60
ataaatatca actgaggcgc gccgtacaaa tcatagaggg tatttaatat gtttcctgcg     120
atgtcattgt ccggattgtt tgcgaatgcg gtgctccggg ctcagcacct gcatcagctg     180
gctgctgaca ccttcaaaga gtttgagcgc acctacatcc cggagggaca gagatactcc     240
atccagaaca cccaggttgc cttctgcttc tctgaaacca tcccggcccc cacgggcaag     300
aatgaggccc agcagaaatc agacttggag ctgcttcgca tctcactgct cctcatccag     360
tcgtggcttg ggcccctgca gttcctcagc agagtcttca ccaacagctt ggtgtttggc     420
acctcggacc gtgtctatga agctgaaga gacctggagg aaggcatcct ggccctgatg     480
cgggagctgg aagatggcac ccccggggct gggcagatcc tcaagcagac ctatgacaaa     540
tttgacacaa acatgcgcag tgacgacgcg ctgctcaaga actacggtct gctctcctgc     600
ttccggaagg acctgcataa gacggagacg tacctgaggg tcatgaagtg ccgccgcttc     660
ggggaggcca gctgcgcctt ctag                                            684

<210> SEQ ID NO 19
<211> LENGTH: 684
<212> TYPE: DNA
<213> ORGANISM: Artificial Sequence
<220> FEATURE:
<223> OTHER INFORMATION: Somatotropin expression vector pXT 536

<400> SEQUENCE: 19
gaattctact gtatgagcat acagttaagg gttgacaacc gatatttatt cacttaatat      60
ataaatatca actgaggcgc gccgtacaaa tcatagaggg tatttaatat gtttccagca     120
atgtcattgt ccggattgtt tgcaaatgcc gtactccggg ctcagcacct gcatcagctg     180
gctgctgaca ccttcaaaga gtttgagcgc acctacatcc cggagggaca gagatactcc     240
atccagaaca cccaggttgc cttctgcttc tctgaaacca tcccggcccc cacgggcaag     300
aatgaggccc agcagaaatc agacttggag ctgcttcgca tctcactgct cctcatccag     360
tcgtggcttg ggcccctgca gttcctcagc agagtcttca ccaacagctt ggtgtttggc     420
acctcggacc gtgtctatga agctgaaga gacctggagg aaggcatcct ggccctgatg     480
cgggagctgg aagatggcac ccccggggct gggcagatcc tcaagcagac ctatgacaaa     540
tttgacacaa acatgcgcag tgacgacgcg ctgctcaaga actacggtct gctctcctgc     600
ttccggaagg acctgcataa gacggagacg tacctgaggg tcatgaagtg ccgccgcttc     660
ggggaggcca gctgcgcctt ctag                                            684

<210> SEQ ID NO 20
<211> LENGTH: 684
<212> TYPE: DNA
<213> ORGANISM: Artificial Sequence
<220> FEATURE:
<223> OTHER INFORMATION: Somatotropin expression vector pXT 541

<400> SEQUENCE: 20
gaattctact gtatgagcat acagttaagg gttgacaacc gatatttatt cacttaatat      60
ataaatatca actgaggcgc gccgtacaaa tcatagaggg tatttaatat gtttccagca     120
atgtcattgt ccggattgtt tgcgaacgcc gtgctccggg ctcagcacct gcatcagctg     180
```

```
gctgctgaca ccttcaaaga gtttgagcgc acctacatcc cggagggaca gagatactcc    240
atccagaaca cccaggttgc cttctgcttc tctgaaacca tcccggcccc cacgggcaag    300
aatgaggccc agcagaaatc agacttggag ctgcttcgca tctcactgct cctcatccag    360
tcgtggcttg ggcccctgca gttcctcagc agagtcttca ccaacagctt ggtgtttggc    420
acctcggacc gtgtctatga aagctgaag gacctggagg aaggcatcct ggccctgatg     480
cgggagctgg aagatggcac ccccgggct gggcagatcc tcaagcagac ctatgacaaa     540
tttgacacaa acatgcgcag tgacgacgcg ctgctcaaga actacggtct gctctcctgc    600
ttccggaagg acctgcataa gacggagacg tacctgaggg tcatgaagtg ccgccgcttc    660
ggggaggcca gctgcgcctt ctag                                           684
```

<210> SEQ ID NO 21
<211> LENGTH: 684
<212> TYPE: DNA
<213> ORGANISM: Artificial Sequence
<220> FEATURE:
<223> OTHER INFORMATION: Somatotropin expression vector pXT 542

<400> SEQUENCE: 21

```
gaattctact gtatgagcat acagttaagg gttgacaacc gatatttatt cacttaatat    60
ataaatatca actgaggcgc gccgtacaaa tcatagaggg tatttaatat gtttcctgca   120
atgtcattgt ccggactttt tgccaacgca gtactccggg ctcagcacct gcatcagctg   180
gctgctgaca ccttcaaaga gtttgagcgc acctacatcc cggagggaca gagatactcc   240
atccagaaca cccaggttgc cttctgcttc tctgaaacca tcccggcccc cacgggcaag   300
aatgaggccc agcagaaatc agacttggag ctgcttcgca tctcactgct cctcatccag   360
tcgtggcttg ggcccctgca gttcctcagc agagtcttca ccaacagctt ggtgtttggc   420
acctcggacc gtgtctatga agctgaag gacctggagg aaggcatcct ggccctgatg     480
cgggagctgg aagatggcac ccccgggct gggcagatcc tcaagcagac ctatgacaaa    540
tttgacacaa acatgcgcag tgacgacgcg ctgctcaaga actacggtct gctctcctgc   600
ttccggaagg acctgcataa gacggagacg tacctgaggg tcatgaagtg ccgccgcttc   660
ggggaggcca gctgcgcctt ctag                                          684
```

<210> SEQ ID NO 22
<211> LENGTH: 684
<212> TYPE: DNA
<213> ORGANISM: Artificial Sequence
<220> FEATURE:
<223> OTHER INFORMATION: Somatotropin expression vector pXT 548

<400> SEQUENCE: 22

```
gaattctact gtatgagcat acagttaagg gttgacaacc gatatttatt cacttaatat    60
ataaatatca actgaggcgc gccgtacaaa tcatagaggg tatttaatat gtttccagca   120
atgtcattgt ccggactctt tgcaaacgcc gtactccggg ctcagcacct gcatcagctg   180
gctgctgaca ccttcaaaga gtttgagcgc acctacatcc cggagggaca gagatactcc   240
atccagaaca cccaggttgc cttctgcttc tctgaaacca tcccggcccc cacgggcaag   300
aatgaggccc agcagaaatc agacttggag ctgcttcgca tctcactgct cctcatccag   360
tcgtggcttg ggcccctgca gttcctcagc agagtcttca ccaacagctt ggtgtttggc   420
acctcggacc gtgtctatga agctgaag gacctggagg aaggcatcct ggccctgatg     480
cgggagctgg aagatggcac ccccgggct gggcagatcc tcaagcagac ctatgacaaa    540
```

```
tttgacacaa acatgcgcag tgacgacgcg ctgctcaaga actacggtct gctctcctgc      600
ttccggaagg acctgcataa gacggagacg tacctgaggg tcatgaagtg ccgccgcttc      660
ggggaggcca gctgcgcctt ctag                                             684

<210> SEQ ID NO 23
<211> LENGTH: 684
<212> TYPE: DNA
<213> ORGANISM: Artificial Sequence
<220> FEATURE:
<223> OTHER INFORMATION: Somatotropin expression vector pXT 549

<400> SEQUENCE: 23
gaattctact gtatgagcat acagttaagg gttgacaacc gatatttatt cacttaatat       60
ataaatatca actgaggcgc gccgtacaaa tcatagaggg tatttaatat gtttcctgca      120
atgtccttgt ccggactttt tgccaatgca gtgctccggg ctcagcacct gcatcagctg      180
gctgctgaca ccttcaaaga gtttgagcgc acctacatcc cggagggaca gagatactcc      240
atccagaaca cccaggttgc cttctgcttc tctgaaacca tcccggcccc cacgggcaag      300
aatgaggccc agcagaaatc agacttggag ctgcttcgca tctcactgct cctcatccag      360
tcgtggcttg ggcccctgca gttcctcagc agagtcttca ccaacagctt ggtgtttggc      420
acctcggacc gtgtctatga aagctgaag gacctggagg aaggcatcct ggccctgatg      480
cgggagctgg aagatggcac ccccgggct gggcagatcc tcaagcagac ctatgacaaa      540
tttgacacaa acatgcgcag tgacgacgcg ctgctcaaga actacggtct gctctcctgc      600
ttccggaagg acctgcataa gacggagacg tacctgaggg tcatgaagtg ccgccgcttc      660
ggggaggcca gctgcgcctt ctag                                             684

<210> SEQ ID NO 24
<211> LENGTH: 684
<212> TYPE: DNA
<213> ORGANISM: Artificial Sequence
<220> FEATURE:
<223> OTHER INFORMATION: Somatotropin expression vector pXT 562

<400> SEQUENCE: 24
gaattctact gtatgagcat acagttaagg gttgacaacc gatatttatt cacttaatat       60
ataaatatca actgaggcgc gccgtacaaa tcatagaggg tatttaatat gtttccagcc      120
atgtcattgt ccggactttt tgccaacgca gtcctccggg ctcagcacct gcatcagctg      180
gctgctgaca ccttcaaaga gtttgagcgc acctacatcc cggagggaca gagatactcc      240
atccagaaca cccaggttgc cttctgcttc tctgaaacca tcccggcccc cacgggcaag      300
aatgaggccc agcagaaatc agacttggag ctgcttcgca tctcactgct cctcatccag      360
tcgtggcttg ggcccctgca gttcctcagc agagtcttca ccaacagctt ggtgtttggc      420
acctcggacc gtgtctatga aagctgaag gacctggagg aaggcatcct ggccctgatg      480
cgggagctgg aagatggcac ccccgggct gggcagatcc tcaagcagac ctatgacaaa      540
tttgacacaa acatgcgcag tgacgacgcg ctgctcaaga actacggtct gctctcctgc      600
ttccggaagg acctgcataa gacggagacg tacctgaggg tcatgaagtg ccgccgcttc      660
ggggaggcca gctgcgcctt ctag                                             684

<210> SEQ ID NO 25
<211> LENGTH: 684
<212> TYPE: DNA
```

<213> ORGANISM: Artificial Sequence
<220> FEATURE:
<223> OTHER INFORMATION: Somatotropin expression vector pXT 576

<400> SEQUENCE: 25

| | | | | | |
|---|---|---|---|---|---|
| gaattctact | gtatgagcat | acagttaagg | gttgacaacc | gatatttatt | cacttaatat | 60 |
| ataaatatca | actgaggcgc | gccgtacaaa | tcatagaggg | tatttaatat | gtttccagca | 120 |
| atgtcattgt | ccggactgtt | tgcgaacgcg | gtgctccggg | ctcagcacct | gcatcagctg | 180 |
| gctgctgaca | ccttcaaaga | gtttgagcgc | acctacatcc | cggagggaca | gagatactcc | 240 |
| atccagaaca | cccaggttgc | cttctgcttc | tctgaaacca | tcccggcccc | cacgggcaag | 300 |
| aatgaggccc | agcagaaatc | agacttggag | ctgcttcgca | tctcactgct | cctcatccag | 360 |
| tcgtggcttg | ggcccctgca | gttcctcagc | agagtcttca | ccaacagctt | ggtgtttggc | 420 |
| acctcggacc | gtgtctatga | gaagctgaag | gacctggagg | aaggcatcct | ggccctgatg | 480 |
| cgggagctgg | aagatggcac | ccccgggct | gggcagatcc | tcaagcagac | ctatgacaaa | 540 |
| tttgacacaa | acatgcgcag | tgacgacgcg | ctgctcaaga | actacggtct | gctctcctgc | 600 |
| ttccggaagg | acctgcataa | gacggagacg | tacctgaggg | tcatgaagtg | ccgccgcttc | 660 |
| ggggaggcca | gctgcgcctt | ctag | | | | 684 |

<210> SEQ ID NO 26
<211> LENGTH: 684
<212> TYPE: DNA
<213> ORGANISM: Artificial Sequence
<220> FEATURE:
<223> OTHER INFORMATION: Somatotropin expression vector pXT 579

<400> SEQUENCE: 26

| | | | | | |
|---|---|---|---|---|---|
| gaattctact | gtatgagcat | acagttaagg | gttgacaacc | gatatttatt | cacttaatat | 60 |
| ataaatatca | actgaggcgc | gccgtacaaa | tcatagaggg | tatttaatat | gtttccagca | 120 |
| atgtcattgt | ccggactttt | tgccaacgcg | gtgctccggg | ctcagcacct | gcatcagctg | 180 |
| gctgctgaca | ccttcaaaga | gtttgagcgc | acctacatcc | cggagggaca | gagatactcc | 240 |
| atccagaaca | cccaggttgc | cttctgcttc | tctgaaacca | tcccggcccc | cacgggcaag | 300 |
| aatgaggccc | agcagaaatc | agacttggag | ctgcttcgca | tctcactgct | cctcatccag | 360 |
| tcgtggcttg | ggcccctgca | gttcctcagc | agagtcttca | ccaacagctt | ggtgtttggc | 420 |
| acctcggacc | gtgtctatga | gaagctgaag | gacctggagg | aaggcatcct | ggccctgatg | 480 |
| cgggagctgg | aagatggcac | ccccgggct | gggcagatcc | tcaagcagac | ctatgacaaa | 540 |
| tttgacacaa | acatgcgcag | tgacgacgcg | ctgctcaaga | actacggtct | gctctcctgc | 600 |
| ttccggaagg | acctgcataa | gacggagacg | tacctgaggg | tcatgaagtg | ccgccgcttc | 660 |
| ggggaggcca | gctgcgcctt | ctag | | | | 684 |

<210> SEQ ID NO 27
<211> LENGTH: 684
<212> TYPE: DNA
<213> ORGANISM: Artificial Sequence
<220> FEATURE:
<223> OTHER INFORMATION: Somatotropin expression vector pXT 580

<400> SEQUENCE: 27

| | | | | | |
|---|---|---|---|---|---|
| gaattctact | gtatgagcat | acagttaagg | gttgacaacc | gatatttatt | cacttaatat | 60 |
| ataaatatca | actgaggcgc | gccgtacaaa | tcatagaggg | tatttaatat | gtttccagca | 120 |
| atgtcattgt | ccggactgtt | tgccaacgcc | gtgctccggg | ctcagcacct | gcatcagctg | 180 |

-continued

```
gctgctgaca ccttcaaaga gtttgagcgc acctacatcc cggagggaca gagatactcc      240
atccagaaca cccaggttgc cttctgcttc tctgaaacca tcccggcccc cacgggcaag      300
aatgaggccc agcagaaatc agacttggag ctgcttcgca tctcactgct cctcatccag      360
tcgtggcttg ggcccctgca gttcctcagc agagtcttca ccaacagctt ggtgtttggc      420
acctcggacc gtgtctatga aagctgaag gacctggagg aaggcatcct ggccctgatg       480
cgggagctgg aagatggcac ccccgggct gggcagatcc tcaagcagac ctatgacaaa       540
tttgacacaa acatgcgcag tgacgacgcg ctgctcaaga actacggtct gctctcctgc      600
ttccggaagg acctgcataa gacggagacg tacctgaggg tcatgaagtg ccgccgcttc      660
ggggaggcca gctgcgcctt ctag                                             684
```

<210> SEQ ID NO 28
<211> LENGTH: 684
<212> TYPE: DNA
<213> ORGANISM: Artificial Sequence
<220> FEATURE:
<223> OTHER INFORMATION: Somatotropin expression vector pXT 581

<400> SEQUENCE: 28

```
gaattctact gtatgagcat acagttaagg gttgacaacc gatatttatt cacttaatat      60
ataaatatca actgaggcgc gccgtacaaa tcatagaggg tatttaatat gtttccagcc      120
atgtccttgt ccggactttt tgccaacgca gtcctccggg ctcagcacct gcatcagctg      180
gctgctgaca ccttcaaaga gtttgagcgc acctacatcc cggagggaca gagatactcc      240
atccagaaca cccaggttgc cttctgcttc tctgaaacca tcccggcccc cacgggcaag      300
aatgaggccc agcagaaatc agacttggag ctgcttcgca tctcactgct cctcatccag      360
tcgtggcttg ggcccctgca gttcctcagc agagtcttca ccaacagctt ggtgtttggc      420
acctcggacc gtgtctatga aagctgaag gacctggagg aaggcatcct ggccctgatg       480
cgggagctgg aagatggcac ccccgggct gggcagatcc tcaagcagac ctatgacaaa       540
tttgacacaa acatgcgcag tgacgacgcg ctgctcaaga actacggtct gctctcctgc      600
ttccggaagg acctgcataa gacggagacg tacctgaggg tcatgaagtg ccgccgcttc      660
ggggaggcca gctgcgcctt ctag                                             684
```

<210> SEQ ID NO 29
<211> LENGTH: 684
<212> TYPE: DNA
<213> ORGANISM: Artificial Sequence
<220> FEATURE:
<223> OTHER INFORMATION: Somatotropin expression vector pXT 584

<400> SEQUENCE: 29

```
gaattctact gtatgagcat acagttaagg gttgacaacc gatatttatt cacttaatat      60
ataaatatca actgaggcgc gccgtacaaa tcatagaggg tatttaatat gtttccagca      120
atgtcattgt ccggactttt tgcgaatgct gtactccggg ctcagcacct gcatcagctg      180
gctgctgaca ccttcaaaga gtttgagcgc acctacatcc cggagggaca gagatactcc      240
atccagaaca cccaggttgc cttctgcttc tctgaaacca tcccggcccc cacgggcaag      300
aatgaggccc agcagaaatc agacttggag ctgcttcgca tctcactgct cctcatccag      360
tcgtggcttg ggcccctgca gttcctcagc agagtcttca ccaacagctt ggtgtttggc      420
acctcggacc gtgtctatga aagctgaag gacctggagg aaggcatcct ggccctgatg       480
```

-continued

```
cgggagctgg aagatggcac ccccccgggct gggcagatcc tcaagcagac ctatgacaaa      540
tttgacacaa acatgcgcag tgacgacgcg ctgctcaaga actacggtct gctctcctgc      600
ttccggaagg acctgcataa gacggagacg tacctgaggg tcatgaagtg ccgccgcttc      660
ggggaggcca gctgcgcctt ctag                                             684
```

<210> SEQ ID NO 30
<211> LENGTH: 685
<212> TYPE: DNA
<213> ORGANISM: Artificial Sequence
<220> FEATURE:
<223> OTHER INFORMATION: Somatotropin expression vector pXT 491

<400> SEQUENCE: 30

```
gaattctact gtatgagcat acagttaagg gttgacaacc gatatttatt cacttaatat       60
ataaatatca actgaggcgc gccagacact aaatagaggg tatttaatta tgtttcctgc      120
catgtccttg tccggattgt ttgcgaatgc ggtcctccgg gctcagcacc tgcatcagct      180
ggctgctgac accttcaaag agtttgagcg cacctacatc ccggagggac agagatactc      240
catccagaac acccaggttg ccttctgctt ctctgaaacc atcccggccc ccacgggcaa      300
gaatgaggcc cagcagaaat cagacttgga gctgcttcgc atctcactgc tcctcatcca      360
gtcgtggctt gggcccctgc agttcctcag cagagtcttc accaacagct tggtgtttgg      420
cacctcggac cgtgtctatg agaagctgaa ggacctggag gaaggcatcc tggccctgat      480
gcgggagctg gaagatggca ccccccgggc tgggcagatc ctcaagcaga cctatgacaa      540
atttgacaca acatgcgcag tgacgacgc gctgctcaag aactacggtc tgctctcctg      600
cttccggaag gacctgcata agacggagac gtacctgagg gtcatgaagt gccgccgctt      660
cggggaggcc agctgcgcct tctag                                            685
```

<210> SEQ ID NO 31
<211> LENGTH: 685
<212> TYPE: DNA
<213> ORGANISM: Artificial Sequence
<220> FEATURE:
<223> OTHER INFORMATION: Somatotropin expression vector pXT 529

<400> SEQUENCE: 31

```
gaattctact gtatgagcat acagttaagg gttgacaacc gatatttatt cacttaatat       60
ataaatatca actgaggcgc gccagacact aaatagaggg tatttaatta tgtttcctgc      120
aatgagcttg tccggattgt ttgcgaatgc ggtgctccgg gctcagcacc tgcatcagct      180
ggctgctgac accttcaaag agtttgagcg cacctacatc ccggagggac agagatactc      240
catccagaac acccaggttg ccttctgctt ctctgaaacc atcccggccc ccacgggcaa      300
gaatgaggcc cagcagaaat cagacttgga gctgcttcgc atctcactgc tcctcatcca      360
gtcgtggctt gggcccctgc agttcctcag cagagtcttc accaacagct tggtgtttgg      420
cacctcggac cgtgtctatg agaagctgaa ggacctggag gaaggcatcc tggccctgat      480
gcgggagctg gaagatggca ccccccgggc tgggcagatc ctcaagcaga cctatgacaa      540
atttgacaca acatgcgcag tgacgacgc gctgctcaag aactacggtc tgctctcctg      600
cttccggaag gacctgcata agacggagac gtacctgagg gtcatgaagt gccgccgctt      660
cggggaggcc agctgcgcct tctag                                            685
```

<210> SEQ ID NO 32
<211> LENGTH: 685

```
<212> TYPE: DNA
<213> ORGANISM: Artificial Sequence
<220> FEATURE:
<223> OTHER INFORMATION: Somatotropin expression vector pXT 530

<400> SEQUENCE: 32
gaattctact gtatgagcat acagttaagg gttgacaacc gatatttatt cacttaatat      60
ataaatatca actgaggcgc gccagacact aaatagaggg tatttaatta tgtttccagc     120
catgtcattg tccggactct ttgcgaatgc ggtcctccgg gctcagcacc tgcatcagct     180
ggctgctgac accttcaaag agtttgagcg cacctacatc ccggagggac agagatactc     240
catccagaac acccaggttg ccttctgctt ctctgaaacc atcccggccc ccacgggcaa     300
gaatgaggcc cagcagaaat cagacttgga gctgcttcgc atctcactgc tcctcatcca     360
gtcgtggctt gggcccctgc agttcctcag cagagtcttc accaacagct tggtgtttgg     420
cacctcggac cgtgtctatg agaagctgaa ggacctggag gaaggcatcc tggccctgat     480
gcgggagctg gaagatggca ccccccgggc tgggcagatc ctcaagcaga cctatgacaa     540
atttgacaca aacatgcgca gtgacgacgc gctgctcaag aactacggtc tgctctcctg     600
cttccggaag gacctgcata agacggagac gtacctgagg gtcatgaagt gccgccgctt     660
cggggaggcc agctgcgcct tctag                                           685

<210> SEQ ID NO 33
<211> LENGTH: 685
<212> TYPE: DNA
<213> ORGANISM: Artificial Sequence
<220> FEATURE:
<223> OTHER INFORMATION: Somatotropin expression vector pXT 619

<400> SEQUENCE: 33
gaattctact gtatgagcat acagttaagg gttgacaacc gatatttatt cacttaatat      60
ataaatatca actgaggcgc gccagacact aaatagaggg tatttaatta tgtttcctgc     120
gatgagcttg tccggattgt ttgcgaatgc agtgctccgg gctcagcacc tgcatcagct     180
ggctgctgac accttcaaag agtttgagcg cacctacatc ccggagggac agagatactc     240
catccagaac acccaggttg ccttctgctt ctctgaaacc atcccggccc ccacgggcaa     300
gaatgaggcc cagcagaaat cagacttgga gctgcttcgc atctcactgc tcctcatcca     360
gtcgtggctt gggcccctgc agttcctcag cagagtcttc accaacagct tggtgtttgg     420
cacctcggac cgtgtctatg agaagctgaa ggacctggag gaaggcatcc tggccctgat     480
gcgggagctg gaagatggca ccccccgggc tgggcagatc ctcaagcaga cctatgacaa     540
atttgacaca aacatgcgca gtgacgacgc gctgctcaag aactacggtc tgctctcctg     600
cttccggaag gacctgcata agacggagac gtacctgagg gtcatgaagt gccgccgctt     660
cggggaggcc agctgcgcct tctag                                           685

<210> SEQ ID NO 34
<211> LENGTH: 685
<212> TYPE: DNA
<213> ORGANISM: Artificial Sequence
<220> FEATURE:
<223> OTHER INFORMATION: Somatotropin expression vector pXT 605

<400> SEQUENCE: 34
gaattctact gtatgagcat acagttaagg gttgacaacc gatatttatt cacttaatat      60
ataaatatca actgaggcgc gccagacact aaatagaggg tatttaatta tgtttccagc     120
```

| | |
|---|---:|
| aatgtccttg tccggactgt ttgcgaacgc agtcctccgg gctcagcacc tgcatcagct | 180 |
| ggctgctgac accttcaaag agtttgagcg cacctacatc ccggagggac agagatactc | 240 |
| catccagaac acccaggttg ccttctgctt ctctgaaacc atcccggccc ccacgggcaa | 300 |
| gaatgaggcc cagcagaaat cagacttgga gctgcttcgc atctcactgc tcctcatcca | 360 |
| gtcgtggctt gggcccctgc agttcctcag cagagtcttc accaacagct tggtgtttgg | 420 |
| cacctcggac cgtgtctatg agaagctgaa ggacctggag gaaggcatcc tggccctgat | 480 |
| gcgggagctg gaagatggca ccccccgggc tgggcagatc ctcaagcaga cctatgacaa | 540 |
| atttgacaca aacatgcgca gtgacgacgc gctgctcaag aactacggtc tgctctcctg | 600 |
| cttccggaag gacctgcata agacggagac gtacctgagg gtcatgaagt gccgccgctt | 660 |
| cggggaggcc agctgcgcct tctag | 685 |

<210> SEQ ID NO 35
<211> LENGTH: 685
<212> TYPE: DNA
<213> ORGANISM: Artificial Sequence
<220> FEATURE:
<223> OTHER INFORMATION: Somatotropin expression vector pXT 606

<400> SEQUENCE: 35

| | |
|---|---:|
| gaattctact gtatgagcat acagttaagg gttgacaacc gatatttatt cacttaatat | 60 |
| ataaatatca actgaggcgc gccagacact aaatagaggg tatttaatta tgtttcctgc | 120 |
| aatgtccttg tccggattgt ttgcgaacgc ggtcctccgg gctcagcacc tgcatcagct | 180 |
| ggctgctgac accttcaaag agtttgagcg cacctacatc ccggagggac agagatactc | 240 |
| catccagaac acccaggttg ccttctgctt ctctgaaacc atcccggccc ccacgggcaa | 300 |
| gaatgaggcc cagcagaaat cagacttgga gctgcttcgc atctcactgc tcctcatcca | 360 |
| gtcgtggctt gggcccctgc agttcctcag cagagtcttc accaacagct tggtgtttgg | 420 |
| cacctcggac cgtgtctatg agaagctgaa ggacctggag gaaggcatcc tggccctgat | 480 |
| gcgggagctg gaagatggca ccccccgggc tgggcagatc ctcaagcaga cctatgacaa | 540 |
| atttgacaca aacatgcgca gtgacgacgc gctgctcaag aactacggtc tgctctcctg | 600 |
| cttccggaag gacctgcata agacggagac gtacctgagg gtcatgaagt gccgccgctt | 660 |
| cggggaggcc agctgcgcct tctag | 685 |

<210> SEQ ID NO 36
<211> LENGTH: 685
<212> TYPE: DNA
<213> ORGANISM: Artificial Sequence
<220> FEATURE:
<223> OTHER INFORMATION: Somatotropin expression vector pXT 607

<400> SEQUENCE: 36

| | |
|---|---:|
| gaattctact gtatgagcat acagttaagg gttgacaacc gatatttatt cacttaatat | 60 |
| ataaatatca actgaggcgc gccagacact aaatagaggg tatttaatta tgtttcctgc | 120 |
| catgtccttg tccggactct ttgccaacgc tgtgctccgg gctcagcacc tgcatcagct | 180 |
| ggctgctgac accttcaaag agtttgagcg cacctacatc ccggagggac agagatactc | 240 |
| catccagaac acccaggttg ccttctgctt ctctgaaacc atcccggccc ccacgggcaa | 300 |
| gaatgaggcc cagcagaaat cagacttgga gctgcttcgc atctcactgc tcctcatcca | 360 |
| gtcgtggctt gggcccctgc agttcctcag cagagtcttc accaacagct tggtgtttgg | 420 |
| cacctcggac cgtgtctatg agaagctgaa ggacctggag gaaggcatcc tggccctgat | 480 |

```
gcgggagctg aagatggca ccccccgggc tgggcagatc ctcaagcaga cctatgacaa      540
atttgacaca acatgcgca gtgacgacgc gctgctcaag aactacggtc tgctctcctg      600
cttccggaag gacctgcata agacggagac gtacctgagg gtcatgaagt gccgccgctt      660
cggggaggcc agctgcgcct tctag                                           685
```

<210> SEQ ID NO 37
<211> LENGTH: 685
<212> TYPE: DNA
<213> ORGANISM: Artificial Sequence
<220> FEATURE:
<223> OTHER INFORMATION: Somatotropin expression vector pXT 620

<400> SEQUENCE: 37

```
gaattctact gtatgagcat acagttaagg gttgacaacc gatatttatt cacttaatat      60
ataaatatca actgaggcgc gccagacact aaatagaggg tatttaatta tgtttcctgc     120
aatgagcttg tccggactt  ttgcgaatgc tgtactccgg gctcagcacc tgcatcagct     180
ggctgctgac accttcaaag agtttgagcg cacctacatc ccggagggac agagatactc     240
catccagaac acccaggttg ccttctgctt ctctgaaacc atcccggccc ccacgggcaa     300
gaatgaggcc cagcagaaat cagacttgga gctgcttcgc atctcactgc tcctcatcca     360
gtcgtggctt gggcccctgc agttcctcag cagagtcttc accaacagct tggtgtttgg     420
cacctcggac cgtgtctatg agaagctgaa ggacctggag gaaggcatcc tggccctgat     480
gcgggagctg aagatggca ccccccgggc tgggcagatc ctcaagcaga cctatgacaa      540
atttgacaca acatgcgca gtgacgacgc gctgctcaag aactacggtc tgctctcctg      600
cttccggaag gacctgcata agacggagac gtacctgagg gtcatgaagt gccgccgctt      660
cggggaggcc agctgcgcct tctag                                           685
```

<210> SEQ ID NO 38
<211> LENGTH: 685
<212> TYPE: DNA
<213> ORGANISM: Artificial Sequence
<220> FEATURE:
<223> OTHER INFORMATION: Somatotropin expression vector pXT 631

<400> SEQUENCE: 38

```
gaattctact gtatgagcat acagttaagg gttgacaacc gatatttatt cacttaatat      60
ataaatatca actgaggcgc gccagacact aaatagaggg tatttaatta tgtttcctgc     120
catgagcttg tccggattgt ttgcaaacgc cgtcctccgg gctcagcacc tgcatcagct     180
ggctgctgac accttcaaag agtttgagcg cacctacatc ccggagggac agagatactc     240
catccagaac acccaggttg ccttctgctt ctctgaaacc atcccggccc ccacgggcaa     300
gaatgaggcc cagcagaaat cagacttgga gctgcttcgc atctcactgc tcctcatcca     360
gtcgtggctt gggcccctgc agttcctcag cagagtcttc accaacagct tggtgtttgg     420
cacctcggac cgtgtctatg agaagctgaa ggacctggag gaaggcatcc tggccctgat     480
gcgggagctg aagatggca ccccccgggc tgggcagatc ctcaagcaga cctatgacaa      540
atttgacaca acatgcgca gtgacgacgc gctgctcaag aactacggtc tgctctcctg      600
cttccggaag gacctgcata agacggagac gtacctgagg gtcatgaagt gccgccgctt      660
cggggaggcc agctgcgcct tctag                                           685
```

<210> SEQ ID NO 39

<211> LENGTH: 685
<212> TYPE: DNA
<213> ORGANISM: Artificial Sequence
<220> FEATURE:
<223> OTHER INFORMATION: Somatotropin expression vector pXT 632

<400> SEQUENCE: 39

| | | |
|---|---|---|
| gaattctact gtatgagcat acagttaagg gttgacaacc gatatttatt cacttaatat | 60 |
| ataaatatca actgaggcgc gccagacact aaatagaggg tatttaatta tgtttccagc | 120 |
| catgtcattg tccggattgt ttgcaaacgc tgtcctccgg gctcagcacc tgcatcagct | 180 |
| ggctgctgac accttcaaag agtttgagcg cacctacatc ccggagggac agagatactc | 240 |
| catccagaac acccaggttg ccttctgctt ctctgaaacc atcccggccc ccacgggcaa | 300 |
| gaatgaggcc cagcagaaat cagacttgga gctgcttcgc atctcactgc tcctcatcca | 360 |
| gtcgtggctt gggcccctgc agttcctcag cagagtcttc accaacagct tggtgtttgg | 420 |
| cacctcggac cgtgtctatg agaagctgaa ggacctggag gaaggcatcc tggccctgat | 480 |
| gcgggagctg aagatggca cccccgggc tgggcagatc ctcaagcaga cctatgacaa | 540 |
| atttgacaca aacatgcgca gtgacgacgc gctgctcaag aactacggtc tgctctcctg | 600 |
| cttccggaag gacctgcata agacggagac gtacctgagg gtcatgaagt gccgccgctt | 660 |
| cggggaggcc agctgcgcct tctag | 685 |

<210> SEQ ID NO 40
<211> LENGTH: 685
<212> TYPE: DNA
<213> ORGANISM: Artificial Sequence
<220> FEATURE:
<223> OTHER INFORMATION: Somatotropin expression vector pXT 633

<400> SEQUENCE: 40

| | | |
|---|---|---|
| gaattctact gtatgagcat acagttaagg gttgacaacc gatatttatt cacttaatat | 60 |
| ataaatatca actgaggcgc gccagacact aaatagaggg tatttaatta tgtttccagc | 120 |
| catgtcattg tccggacttt ttgcgaacgc tgtgctccgg gctcagcacc tgcatcagct | 180 |
| ggctgctgac accttcaaag agtttgagcg cacctacatc ccggagggac agagatactc | 240 |
| catccagaac acccaggttg ccttctgctt ctctgaaacc atcccggccc ccacgggcaa | 300 |
| gaatgaggcc cagcagaaat cagacttgga gctgcttcgc atctcactgc tcctcatcca | 360 |
| gtcgtggctt gggcccctgc agttcctcag cagagtcttc accaacagct tggtgtttgg | 420 |
| cacctcggac cgtgtctatg agaagctgaa ggacctggag gaaggcatcc tggccctgat | 480 |
| gcgggagctg aagatggca cccccgggc tgggcagatc ctcaagcaga cctatgacaa | 540 |
| atttgacaca aacatgcgca gtgacgacgc gctgctcaag aactacggtc tgctctcctg | 600 |
| cttccggaag gacctgcata agacggagac gtacctgagg gtcatgaagt gccgccgctt | 660 |
| cggggaggcc agctgcgcct tctag | 685 |

<210> SEQ ID NO 41
<211> LENGTH: 685
<212> TYPE: DNA
<213> ORGANISM: Artificial Sequence
<220> FEATURE:
<223> OTHER INFORMATION: Somatotropin expression vector pXT 635

<400> SEQUENCE: 41

| | | |
|---|---|---|
| gaattctact gtatgagcat acagttaagg gttgacaacc gatatttatt cacttaatat | 60 |
| ataaatatca actgaggcgc gccagacact aaatagaggg tatttaatta tgtttcctgc | 120 |

-continued

```
catgtcattg tccggacttt ttgccaatgc ggtcctccgg gctcagcacc tgcatcagct        180
ggctgctgac accttcaaag agtttgagcg cacctacatc ccggagggac agagatactc        240
catccagaac acccaggttg ccttctgctt ctctgaaacc atcccggccc cacgggcaa         300 gaatgaggcc cagcagaaat cagacttgga gctgcttcgc atctcactgc tcctcatcca        360
gtcgtggctt gggcccctgc agttcctcag cagagtcttc accaacagct tggtgtttgg       420
cacctcggac cgtgtctatg agaagctgaa ggacctggag aaggcatcc tggccctgat         480 gcgggagctg aagatggca ccccccgggc tgggcagatc ctcaagcaga cctatgacaa         540
atttgacaca aacatgcgca gtgacgacgc gctgctcaag aactacggtc tgctctcctg        600
cttccggaag gacctgcata agacggagac gtacctgagg gtcatgaagt gccgccgctt       660
cggggaggcc agctgcgcct tctag                                               685
```

<210> SEQ ID NO 42
<211> LENGTH: 685
<212> TYPE: DNA
<213> ORGANISM: Artificial Sequence
<220> FEATURE:
<223> OTHER INFORMATION: Somatotropin expression vector pXT 681

<400> SEQUENCE: 42

```
gaattctact gtatgagcat acagttaagg gttgacaacc gatatttatt cacttaatat        60
ataaatatca actgaggcgc gccagacact aaatagaggg tatttaatta tgttcccagc       120
catgtcattg tccggacttt ttgccaacgc ggtgctccgg gctcagcacc tgcatcagct        180
ggctgctgac accttcaaag agtttgagcg cacctacatc ccggagggac agagatactc        240
catccagaac acccaggttg ccttctgctt ctctgaaacc atcccggccc cacgggcaa         300 gaatgaggcc cagcagaaat cagacttgga gctgcttcgc atctcactgc tcctcatcca        360
gtcgtggctt gggcccctgc agttcctcag cagagtcttc accaacagct tggtgtttgg       420
cacctcggac cgtgtctatg agaagctgaa ggacctggag aaggcatcc tggccctgat         480 gcgggagctg aagatggca ccccccgggc tgggcagatc ctcaagcaga cctatgacaa         540
atttgacaca aacatgcgca gtgacgacgc gctgctcaag aactacggtc tgctctcctg        600
cttccggaag gacctgcata agacggagac gtacctgagg gtcatgaagt gccgccgctt       660
cggggaggcc agctgcgcct tctag                                               685
```

<210> SEQ ID NO 43
<211> LENGTH: 684
<212> TYPE: DNA
<213> ORGANISM: Artificial Sequence
<220> FEATURE:
<223> OTHER INFORMATION: Somatotropin expression vector pXT 483

<400> SEQUENCE: 43

```
gaattctact gtatgagcat acagttaagg gttgacaacc gatatttatt cacttaatat        60
ataaatatca actgaggcgc gcctaaaaga gactaggagg agattagaat gttcccagca       120
atgagtttgt ccggactgtt tgcgaacgcc gtgctccggg ctcagcacct gcatcagctg        180
gctgctgaca ccttcaaaga gtttgagcgc acctacatcc cggagggaca gagatactcc        240
atccagaaca cccaggttgc cttctgcttc tctgaaacca tcccggcccc cacgggcaag       300
aatgaggccc agcagaaatc agacttggag ctgcttcgca tctcactgct cctcatccag       360
tcgtggcttg ggcccctgca gttcctcagc agagtcttca ccaacagctt ggtgtttggc       420
```

```
acctcggacc gtgtctatga agctgaag gacctggagg aaggcatcct ggccctgatg      480
cgggagctgg aagatggcac cccccgggct gggcagatcc tcaagcagac ctatgacaaa      540
tttgacacaa acatgcgcag tgacgacgcg ctgctcaaga actacggtct gctctcctgc      600
ttccggaagg acctgcataa gacggagacg tacctgaggg tcatgaagtg ccgccgcttc      660
ggggaggcca gctgcgcctt ctag                                             684
```

<210> SEQ ID NO 44
<211> LENGTH: 684
<212> TYPE: DNA
<213> ORGANISM: Artificial Sequence
<220> FEATURE:
<223> OTHER INFORMATION: Somatotropin expression vector pXT 564

<400> SEQUENCE: 44

```
gaattctact gtatgagcat acagttaagg gttgacaacc gatatttatt cacttaatat      60
ataaatatca actgaggcgc gcctaaaaga gactaggagg agattagaat gttcccagca     120
atgtcattgt ccggactgtt tgccaatgcg gtcctccggg ctcagcacct gcatcagctg     180
gctgctgaca ccttcaaaga gtttgagcgc acctacatcc cggagggaca gagatactcc     240
atccagaaca cccaggttgc cttctgcttc tctgaaacca tcccggcccc cacgggcaag     300
aatgaggccc agcagaaatc agacttggag ctgcttcgca tctcactgct cctcatccag     360
tcgtggcttg ggcccctgca gttcctcagc agagtcttca ccaacagctt ggtgtttggc     420
acctcggacc gtgtctatga agctgaag gacctggagg aaggcatcct ggccctgatg      480
cgggagctgg aagatggcac cccccgggct gggcagatcc tcaagcagac ctatgacaaa      540
tttgacacaa acatgcgcag tgacgacgcg ctgctcaaga actacggtct gctctcctgc      600
ttccggaagg acctgcataa gacggagacg tacctgaggg tcatgaagtg ccgccgcttc      660
ggggaggcca gctgcgcctt ctag                                             684
```

<210> SEQ ID NO 45
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 45

```
cataacatca agaggatatg aaatt                                            25
```

<210> SEQ ID NO 46
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 46

```
gtacaaatca tagagggtat ttaat                                            25
```

<210> SEQ ID NO 47
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 47

```
agacactaaa tagagggtat ttaatt                                           26
```

<210> SEQ ID NO 48
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 48
taaaagagac taggaggaga ttaga                                       25

<210> SEQ ID NO 49
<211> LENGTH: 983
<212> TYPE: DNA
<213> ORGANISM: Artificial Sequence
<220> FEATURE:
<223> OTHER INFORMATION: Synthetic construct for expression of bovine
      somatotropin

<400> SEQUENCE: 49
gaattctact gtatgagcat acagttaagg gttgacaacc gatatttatt cacttaatat    60
ataaatatca actgaggcgc gcccataaca tcaagaggat atgaaattat gtttccagcc   120
atgagcttgt ccggactctt tgccaatgct gtactccggg ctcagcacct gcatcagctg   180
gctgctgaca ccttcaaaga gtttgagcgc acctacatcc cggagggaca gagatactcc   240
atccagaaca cccaggttgc cttctgcttc tctgaaacca tcccggcccc cacgggcaag   300
aatgaggccc agcagaaatc agacttggag ctgcttcgca tctcactgct cctcatccag   360
tcgtggcttg ggcccctgca gttcctcagc agagtcttca ccaacagctt ggtgtttggc   420
acctcggacc gtgtctatga aagctgaag gacctggagg aaggcatcct ggccctgatg   480
cgggagctgg aagatggcac ccccgggct gggcagatcc tcaagcagac ctatgacaaa   540
tttgacacaa acatgcgcag tgacgacgcg ctgctcaaga actacggtct gctctcctgc   600
ttccggaagg acctgcataa gacggagacg tacctgaggg tcatgaagtg ccgccgcttc   660
ggggaggcca gctgcgcctt ctagaagctt aattctcact cattaggcac cccaggcttt   720
acactttatg cttccggctc gtataatgtg tggaattgtg agcggataac aatttcacac   780
aggaaacagc tgattgccct tcaccgcctg gcctccgttg agccatctgg atcggcagcg   840
ttgtcttcat caaccggaac gagcatgccg gagagcagct cactcattag caccccagg   900 ctttacactt tatgcttccg gctcgtataa tgtgtggaat tgtgagcgga taacaatttc   960
acacaggaaa cagaattaag ctt                                          983

<210> SEQ ID NO 50
<211> LENGTH: 977
<212> TYPE: DNA
<213> ORGANISM: Artificial Sequence
<220> FEATURE:
<223> OTHER INFORMATION: Synthetic construct for expression of bovine
      somatotropin

<400> SEQUENCE: 50
gaattctact gtatgagcat acagttaagg gttgacaacc gatatttatt cacttaatat    60
ataaatatca actgaggcgc gcccataaca tcaagaggat atgaaattat gtttccagcc 120
atgagcttgt ccggactctt tgccaatgct gtactccggg ctcagcacct gcatcagctg 180
gctgctgaca ccttcaaaga gtttgagcgc acctacatcc cggagggaca gcgttactcc 240
atccagaaca cccaggttgc cttctgcttc tctgaaacca tcccggcccc gacgggcaag 300

-continued

```
aatgaggccc agcagaaatc agacttggag ctgcttcgca tctcactgct cctcatccag    360
agctggcttg ggccgctgca gttcctcagc cgtgtcttca ccaacagctt ggtgtttggc    420
accagcgacc gtgtctatga gaagctgaag gacctggagg aaggcatcct ggccctgatg    480
cgtgagctgg aagatggcac cccgcgtgct gggcagatcc tcaagcagac ctatgacaaa    540
tttgacacaa acatgcgcag tgacgacgcg ctgctcaaga actacggtct gctctcctgc    600
ttccgtaagg acctgcataa gacggagacg tacctgcgtg tcatgaagtg ccgccgcttc    660
ggggaggcga gctgcgcctt ctaatagctc gagtctagac tcactcatta ggcaccccag    720
gctttacact ttatgcttcc ggctcgtata atgtgtggaa ttgtgagcgg ataacaattt    780
cacacaggaa aaagctgatt gcccttcacc gcctggcctc cgttgagcca tctggatcgg    840
cagcgttgtc ttcatcaacc ggaacgagca tgccggagag cagctcactc attaggcacc    900
ccaggcttta cactttatgc ttccggctcg tataatgtgt ggaattgtga gcggataaca    960
atttcacaca gaagctt                                                   977
```